United States Patent [19]

Cook

[11] 4,439,604

[45] Mar. 27, 1984

[54] 7-β-D-ARABINOFURANOSYL-7H-PYRROLO[2,3-D]PYRIMIDINE COMPOUNDS AND METHODS FOR THEIR PRODUCTION

[75] Inventor: P. Dan Cook, Ann Arbor, Mich.

[73] Assignee: Warner-Lambert Company, Morris Plains, N.J.

[21] Appl. No.: 391,806

[22] Filed: Jun. 24, 1982

Related U.S. Application Data

[62] Division of Ser. No. 229,471, Jan. 29, 1981, Pat. No. 4,352,795.

[51] Int. Cl.³ .......................................... C07H 19/16
[52] U.S. Cl. ....................................................... 536/24
[58] Field of Search .................... 536/24, 22, 25, 18.7, 536/23, 55.3

[56] References Cited

U.S. PATENT DOCUMENTS 3,501,456  3/1970  Shen et al. ............................. 536/24
3,992,531  11/1976  Prasad et al. ......................... 536/24
4,352,795  10/1982  Cook ..................................... 536/24

OTHER PUBLICATIONS

Tolman et al., "Pyrrolopyrimidine Nucleosides. VI", vol. 7, pp. 799–806, Aug. 1970.

Primary Examiner—Johnnie R. Brown
Attorney, Agent, or Firm—Jerry F. Janssen

[57] ABSTRACT

Hydroxy, amino and sulfhydryl derivatives of 7-β-D-arabinofuranosyl-7H-pyrrolo[2,3-d]pyrimidine, their corresponding esters and non-toxic pharmaceutically acceptable salts are produced by arabinofuranosylation of the requisite heterocycles with 2,3,5-tri-O-benzyl-α-D-arabinofuranosyl halide and further reaction to obtain the desired compounds. These water soluble compounds are resistant to adenosine deaminase and exhibit antiviral activity.

1 Claim, No Drawings

7-β-D-ARABINOFURANOSYL-7H-PYRROLO[2,3-d]PYRIMIDINE COMPOUNDS AND METHODS FOR THEIR PRODUCTION

This is a division of application Ser. No. 229,471, filed Jan. 29, 1981, now U.S. Pat. No. 4,352,795.

SUMMARY OF THE INVENTION

The present invention relates to novel 7-β-D-arabinofuranosyl-7H-pyrrolo[2,3-d]pyrimidines that are useful antiviral agents and to the method for their production. More particularly, the invention relates to novel hydroxy, amino and sulfhydryl derivatives of 7-β-D-arabinofuranosyl-7H-pyrrolo[2,3-d]pyrimidine compounds that are represented by the formula

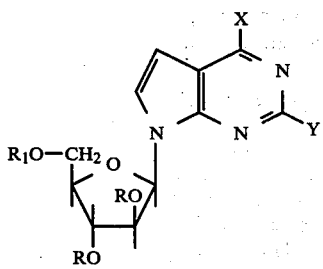

and the pharmaceutically acceptable salts thereof wherein when Y is hydrogen or $NH_2$, X is $NH_2$, OH or SH; R is hydrogen or acyl containing 2 to 6 carbon atoms; and $R_1$ is hydrogen, acyl containing 2 to 6 carbon atoms or phosphate.

The preferred compounds of the present invention are designated:

7-β-D-arabinofuranosyl-7H-pyrrolo[2,3-d]pyrimidin-4-amine 5'-phosphate;

7-β-D-arabinofuranosyl-3,7-dihydro-4H-pyrrolo[2,3-d]pyrimidin-4-one;

7-β-D-arabinofuranosyl-3,7-dihydro-4H-pyrrolo[2,3-d]pyrimidin-4-one 5'-phosphate;

7-(2,3,5-tri-O-acetyl-β-D-arabinofuranosyl)-7H-pyrrolo-[2,3-d]pyrimidin-4-amine;

7-β-D-arabinofuranosyl-3,7-dihydro-4H-pyrrolo[2,3-d]pyrimidine-4-thione;

7β-D-arabinofuranosyl-7H-pyrrolo[2,3-d]pyrimidine;

7-β-D-arabinofuranosyl-7H-pyrrolo[2,3-d]pyrimidine-2,4-diamine;

7-β-D-arabinofuranosyl-7H-pyrrolo[2,3-d]pyrimidine-2,4-diamine 5'-phosphate;

2-amino-7-β-D-arabinofuranosyl-3,7-dihydro-4H-pyrrolo-[2,3-d-]pyrimidin-4-one;

2-amino-7-β-D-arabinofuranosyl-3,7-dihydro-4H-pyrrolo-[2,3-d]pyrimidin-4-one 5'-phosphate; and pharmaceutically acceptable salts thereof.

In accordance with the invention, compounds having the formula

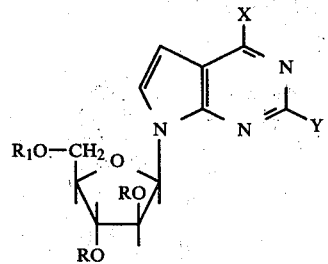

wherein X, Y, R and $R_1$ are as defined above are produced by treating the corresponding 4-chloro-7H-pyrrolo[2,3-d]pyrimidine with sodium hydride in a suitable solvent to form the anion having the formula

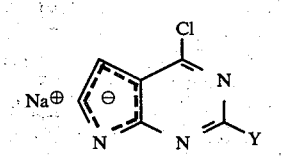

and glycosylating said anion with 2,3,5-tri-O-benzyl-α-D-arabinofuranosyl chloride.

The present, novel coupling process overcomes the difficulties and shortcomings prominent in the prior art. A preferred anion of the heterocycle in dimethylformamide (DMF) is utilized to increase nucleophilicity and solubility. The chlorine atom of the tribenzylarabinofuranosyl chloride is converted into sodium chloride. Coupling is completed at ambient temperatures, usually within 0.5 hour. What was unpredicted in this process was that, although a very polar solvent was used, which would tend to favor sugar anomerization and thus approximately equal amounts of the and nucleosides would be expected, coupling under these conditions was rapid and preferentially took place before significant anomerization occurred. This relatively simple process provided high yields of the β-nucleoside. Anion formation of the requisite heterocycles is obtained by treating the heterocycle dissolved in dry DMF with sodium hydride. The anion formation requires approximately 10–15 minutes rather than 12–20 hours of reflux in hexamethyldisilazane or acetonitrile and bissilytrifluoroacetamide and then distillation to obtain a silylated heterocycle. Other anion formation procedures employing different bases and polar solvents may be used; however, sodium hydride in DMF is preferred due to its experimental simplicity.

The use of anionic heterocycles in DMF or other polar solvents greatly increases the nucleophilicity to the heterocycle and allows the use of heterocycles possessing a variety of substituents. This latter advantage is particularly important since proper choice and positioning of substituents may be utilized to direct the arabinofuranosyl group to the desired site in the heterocycle. A polar solvent such as DMF is essential to solubilize the anionic heterocycle.

The resulting blocked 4-chloronucleoside is converted to the corresponding blocked 4-amino-β-D-arabinofuranosylnucleoside by treatment with excess hydrazine to form the corresponding 4-hydrazino derivative. The crude 4-hydrazinonucleoside, without any purification, is hydrogenolyzed with Raney nickel to produce the corresponding blocked 4-aminonucleoside. The blocking groups are removed by conventional means such as reduction with sodium in liquid ammonia. Recrystallization from water provides the desired unblocked 4-aminonucleoside.

The 4-aminonucleoside is converted to the 2,3,5-tri-O-acetyl compound; the 5'-phosphate compound; and the 3,7-dihydro-4H-pyrrolo[2,3-d]pyrimidin-4-one compound by treatment with acetic anhydride, phosphoryl chloride in triethylphosphate, and sodium nitrite, respectively. The 4-aminonucleoside 5'-phosphate is treated with sodium nitrite to produce the corresponding 3,7-dihydro-4H-pyrrolo[2,3-d]pyrimidin-4-one 5'-phosphate.

The above 3,7-dihydro-4H-pyrrolo[2,3-d]pyrimidin-4-one compound, after conversion to the 2,3,5-tri-O-acetyl derivative, and sequential treatment with phosphorus pentasulfide and deblocking results in the corresponding 3,7-dihydro-4H-pyrrolo[2,3-d]pyrimidin-4-thione. Treatment of the 3,7-dihydro-4H-pyrrolo-[2,3-d]pyrimidin-4-thione with Raney nickel provides 7-β-D-arabinofuranosyl-7H-pyrrolo[2,3-d]pyrimidine.

4-Chloro-2-methylmercapto-7-(2,3,5-tri-O-benzyl-β-D-arabinofuranosyl)-7H-pyrrolo[2,3-d]pyrimidine, obtained by glycosylating the anion of 4-chloro-2-methylmercapto-7H-pyrrolo[2,3-d]pyrimidine with 2,3,5-tri-O-benzyl-α-D-arabinofuranosyl chloride, is oxidized to obtain 4-chloro-2-methylsulfonyl-7-(2,3,5-tri-O-benzyl-β-D-arabinofuranosyl)-7H-pyrrolo[2,3-d]pyrimidine. The 2-methylsulfonyl compound is sequentially treated with hydrazine and Raney nickel to obtain 7-β-D-arabinofuranosyl-7H-pyrrolo[2,3-d]pyrimidine-2,4-diamine. The corresponding 5'-phosphate is obtained by treatment with triethyl phosphate and phosphoryl chloride.

4-Chloro-2-methylsulfonyl-7-(2,3,5-tri-O-benzyl-β-D-arabinofuranosyl)-7H-pyrrolo[2,3,5-d]pyrimidine reacted sequentially with sodium allyloxide and liquid ammonia and deblocked by hydrogenation in the presence of a catalyst provides 2-amino-7-β-D-arabinofuranosyl-3,7-dihydro-4H-pyrrolo[2,3-d]pyrimidine-4-one. Treatment with phosphoryl chloride and triethyl phosphate provides the corresponding 5'-phosphate compound.

The heterocycles required as starting material in the foregoing process can be prepared by any of a variety of methods. This general class of compounds and a number of individual members of the class have been reported.

The synthesis of 4-chloro-7H-pyrrolo[2,3-d]pyrimidine is described by Dovoll in J. Chem. Soc., 131 (1960). The synthesis of 4-chloro-2-methylmercapto-7H-pyrrolo[2,3-d]pyrimidine is described by C. W. Noell and R. K. Robins in J. Heterocyclic Chem., 1, 34 (1964).

The requisite sugar, 2,3,5-tri-O-benzyl-α-D-arabinofuranosyl chloride is prepared according to C. P. J. Glaudemans, et al., J. Am. Chem. Soc., 87, 4636 (1965).

Pharmaceutically acceptable salts can be produced by dissolving the nucleosides in water containing one equivalent of the appropriate acid. The aqueous solution is concentrated in vacuo and the residue is recrystallized from ethanol-water mixtures.

The products of the phosphorylation reactions set forth above may be isolated in the free acid form or in salt form by appropriate adjustment of the pH with a suitable base. The initial free acid product is first adsorbed on activated charcoal and then converted to the diammonium salt by eluting the charcoal with a solvent mixture made up of ethanol, water, and ammonium hydroxide. The diammonium salt can then be converted back to the free acid by ion exchange techniques, or it can be converted to other salts by direct reaction with suitable salt forming substances.

The various salts comprehended within the present invention include those formed with the ammonium ion, alkali metal cations, and alkaline earth metal cations. These salts and the corresponding free acid may differ in certain physical properties, but they are otherwise equivalent for purposes of the invention.

The amino, hydroxy, and sulfhydryl derivatives of 7-β-D-arabinofuranosyl-7H-pyrrolo[2,3-d]pyrimidine and their sugar esters are novel chemical compounds that are useful as antiviral agents against Herpes virus.

Their activity as antiviral agents can be quantitatively measured in an in vitro test by utilizing the plaque reduction technique first developed by Dulbecco (Proc. Natl. Acad. Sci., Volume 38, pages 747–752) and modified by Hsiung and Melnick [Virology, Volume 1, pages 533–535 (1955)]. In this test, a complete cell monolayer is first grown on a glass test unit. The growth medium is then removed, and the virus is adsorbed on the cell monolayer for a measured time period. In the absence of an antiviral agent, the virus will destroy well-defined areas of cells, called plaques, that can be seen microscopically when the viral stain, neutral red, is added to the system. To test the inhibiting effect of a given compound, the test compound in solution is added to the virus-cell system, and the whole is covered with a nutrient agar overlay containing neutral red. After incubation, the plaques are counted, and the number of plaques produced in the system containing the test compound is compared with the number produced in the control systems, from which only the test compound is omitted. The inhibitory activity of a test compound is reported as the percentage reduction of the plaque count on the test units compared with that on the controls.

When tested by this plaque reduction technique, with 4 oz. glass bottles serving as the test units and H. Ep. No. 2 cells making up the cell monolayer, the preferred compounds of the invention, in Hank's Balanced Salt Solution (pH 7–8), typically are found to give substantial plaque reduction against Herpes simplex.

The compounds of the present invention are administered parenterally, preferably intravenously. Injectable solutions are given so as to provide the host with from 0.0005 mg to 5 mg of the compound of this invention per kg of body weight per day. The preferred quantity which is administered on a daily basis is from about 0.005 mg to 2 mg of the compound of this invention per kg of body weight.

The pharmaceutical composition may be in bulk from containing 0.005 to 2 parts of the compound of this invention which is placed in solution at time of use by the addition of a solvent which is appropriate for injectables. In the alternative, the pharmaceutical composition may be an aqueous solution containing 0.005 to 2 parts of the compound of this invention and other materials such as preservatives, buffering agents, agents intended to adjust the isotonicity of the solution, etc. The volume of water is not critical and may vary from less than 1 ml to about 500 ml.

In addition, the compounds of the present invention may be employed in ophthalmic compositions, such as ointments and solutions, in the treatment of Herpes keratitis. Thus ointments or solutions containing about 0.001 to 0.5 percent, preferably 0.001 to 0.05 percent of the compound of this invention in a suitable pharmaceutical carrier may be employed. In addition, preservatives, agents intended to adjust isotonicity of the solution, buffers, etc., may be incorporated into the pharmaceutical carriers.

Lastly, the compounds of the present invention may also be employed in topical ointments and creams. The ointment or cream should contain about 0.001 to 0.5 percent, preferably 0.001 to 0.05 percent of the compound of this invention in a suitable pharmaceutical carrier which may optionally contain preservatives, coloring agents, etc.

The invention is illustrated by the following examples.

EXAMPLE 1

7-β-D-Arabinofuranosyl-7H-pyrrolo[2,3-d]pyrimidin-4-amine

Method A

4-Chloro-7-(2,3,5-tri-O-benzyl-β-D-arabinofuranosyl)-7H-pyrrolo[2,3-d]pyrimidine.

A suspension of 240 mg of sodium hydride, 1.54 g of 4-chloro-7H-pyrrolo[2,3-d]pyrimidine, and 6 ml of dry dimethyl-formamide (DMF) is stirred at 50° C. for 15 minutes, cooled, and added to 4.83 g of 2,3,5-tri-O-benzyl-α-D-arabinofuranosyl chloride in 4 ml of DMF. The solution is stirred at ambient temperature for two hours, concentrated in vacuo, and distributed between a mixture of ethyl acetate-water. Chromatography of the dried ethyl acetate layer over silica gel with 4:1 benzene-ethyl acetate provides 3.3 g of yellow, syrupy 4-chloro-7-(2,3,5-tri-O-benzyl-β-D-arabinofuranosyl)-7H-pyrrolo[2,3-d]pyrimidine.

7-(2,3,5-Tri-O-benzyl-β-arabinofuranosyl)-7H-pyrrolo[2,3-d]pyrimidin-4-amine.

A mixture of 3 g of 4-chloro-7-(2,3,5-tri-O-benzyl-β-D-arabinofuranosyl)-7H-pyrrolo[2,3-d]pyrimidine, 3 ml of methanol, and 20 ml of liquid ammonia is placed in a stainless steel reactor and heated at 100° C. for 5 hours. The ammonia is allowed to evaporate and the residue, after evaporation of the methanol, is distributed between ethyl acetate and water. The aqueous layer is reextracted with ethyl acetate and the dried (MgSO$_4$) ethyl acetate solution is evaporated in vacuo to provide 2.6 g of 7-(2,3,5tri-O-benzyl-β-D-arabinofuranosyl)-7H-pyrrolo[2,3-d]pyrimidin-4-amine as a crude yellow syrup. Chromatography of this material over silica gel with ethyl acetate provides 2.6 g of pure product as a colorless syrup.

7-β-D-Arabinofuranosyl-7H-pyrrolo[2,3-d]pyrimidin-4-amine.

A mixture of 2.5 g of 7-(2,3,5-tri-O-benzyl-β-D-arabinofuranosyl)-7H-pyrrolo[2,3-d]pyrimidin-4-amine, 5 ml of acetic acid, 500 mg of 20% palladium on charcoal, and 95 ml of methoxyethanol is hydrogenated at 50°-55° C. and approximately 3 atmospheres until uptake of hydrogen ceases. The mixture is filtered, evaporated in vacuo, and coevaporated with xylenes to provide a red syrup which is dissolved in water and treated with Amberlite ion exchange resin (20 ml of wet IR-45). The resin is filtered and washed several times with boiling water. The combined filtrates are evaporated in vacuo to provide 992 mg of crude 7-β-D-arabinofuranosyl-7H-pyrrolo[2,3-d]pyrimidin-4-amine. Recrystallization of this material from water provides 800 mg of product, m.p. 117°-120° C. (after drying at 100° C. for one hour); $[\alpha]_D^{25} = +16.2$ (1.02% in H$_2$O).

Method B

4-Chloro-2-methylmercapto-7-(2,3,5-tri-O-benzyl-β-D-arabinofuranosyl)-7H-pyrrolo[2,3-d]pyrimidine.

A suspension of 3.1 g sodium hydride, 25.9 g of 4-chloro-2-methylmercapto-7H-pyrrolo[2,3-d]pyrimidine, and 250 ml of dry dimethylformamide (DMF) is stirred at 50° C. for 0.5 hour, cooled, and added to 62.8 g of 2,3,5-tri-O-benzyl-α-D-arabinofuranosyl chloride. The solution is stirred at ambient temperature for 15 hours, concentrated in vacuo, and distributed between a mixture of ethyl acetate and water. Chromatography of the dried (MgSO$_4$) layer over silica gel with 4:1 toluene-ethyl acetate provides 76 g of yellow, syrupy 4-chloro-2-methylmercapto-7-(2,3,5-tri-O-benzyl-β-D-arabinofuranosyl)-7H-pyrrolo[2,3-d]pyrimidine.

4-Hydrazino-2-methylmercapto-7-(2,3,5-tri-O-benzyl-β-D-arabinofuranosyl)-7H-pyrrolo[2,3-d]-pyrimidine.

A mixture of 55 g of 4-chloro-2-methylmercapto-7-(2,3,5-tri-O-benzyl-β-D-arabinofuranosyl)-7H-pyrrolo[2,3-d]pyrimidine and 500 ml of anhydrous hydrazine is heated under reflux and a nitrogen atmosphere for two hours, evaporated in vacuo, and coevaporated with xylenes. The residue is distributed between a mixture of ethyl acetate and water and the aqueous layer reextracted with ethyl acetate. The dried ethyl acetate extracts are combined and evaporated in vacuo to provide 51 g of crude syrupy product. Chromatography of this material over silica gel and ethyl acetate provides 49 g of pure 4-hydrazino-2-methylmercapto-7-(2,3,5-tri-O-benzyl-β-D-arabinofuranosyl)-7H-pyrrolo[2,3-d]pyrimidine as a yellow syrup.

4-Hydrazino-7-(2,3,5-tri-O-benzyl-β-D-arabinofuranosyl)-7H-pyrrolo[2,3-d]pyrimidine.

A mixture of 10 g of 4-chloro-7-(2,3,5-tri-O-benzyl-β-D-arabinofuranosyl)-7H-pyrrolo[2,3-d]pyrimidine and 100 ml of anhydrous hydrazine is heated under reflux and a nitrogen atmosphere for one hour, evaporated in vacuo, and coevaporated with xylenes. The residue is distributed between a mixture of ethyl acetate and water. The aqueous layer is reextracted with ethyl acetate and the dried ethyl acetate solution is evaporated in vacuo to provide 9.0 g of crude product. Purification of this material by silica gel chromatography (ethyl acetate) provides pure 4-hydrazino-7-(2,3,5-tri-O-benzyl-β-D-arabinofuranosyl)-7H-pyrrolo[2,3-d]pyrimidine as a yellow syrup.

7-(2,3,5-Tri-O-benzyl-β-D-arabinofuranosyl)-7H-pyrrolo[2,3-d]pyrimidin-4-amine.

A mixture of 48 g of 4-hydrazino-2-methylmercapto-7-(2,3,5-tri-O-benzyl-β-D-arabinofuranosyl)-7H-pyrrolo[2,3-d]pyrimidine, 500 ml of ethanol, and 100 g of Raney nickel suspension is stirred and heated under reflux for one hour. An additional 100 g of Raney nickel is added and stirring and heating is continued for two hours. The hot suspension is filtered and the filter cake is washed with ethyl acetate. The combined dried filtrates are evaporated in vacuo to 43 g of dark syrup. Chromatography of this material over silica gel with ethyl acetate provides 33 g of pure 7-(2,3,5-tri-O-benzyl-β-D-arabinofuranosyl)-7H-pyrrolo[2,3-d]pyrimidin-4-amine. The same compound may also be obtained by hydrogenolysis of 4-hydrazine-7-(2,3,5-tri-O-benzyl-β-D-arabinofuranosyl)-7H-pyrrolo[2,3-d]pyrimidine with Raney nickel.

EXAMPLE 2

7-β-D-Arabinofuranosyl-7H-pyrrolo[2,3-d]pyrimidin-4-amine 5'-Phosphate

A mixture of 8 g of 7-β-D-arabinofuranosyl-7H-pyrrolo[2,3-d]pyrimidin-4-amine, 80 ml of triethyl phosphate, and 6.0 g of phosphoryl chloride is stirred at 0°-5° C. for 4.5 hours at which point an additional two g of phosphoryl chloride is added and stirring is continued for one hour. The solution is poured into 300 ml of crushed ice and the pH is adjusted by the addition of solid sodium hydrogen carbonate until it stabilizes at pH 5-6. The solution is extracted with chloroform and concentrated in vacuo until crystallization begins. Water is added to achieve a solution and the pH is readjusted to 6-7 with solid sodium hydrogen carbonate. The solution is placed on Dowex 1×2 50-100 mesh (formate) column (400 ml of wet resin) and is washed with water until the eluate is salt-free. Gradient elution (water to 0.1 M formic acid) gives the pure product. Appropriate fractions are evaporated in vacuo, keeping the temperature below 30° C., to a small volume. Addition of hot ethanol, until the cloud point is obtained, allows crystallization to proceed several hours later providing pure 7-β-arabinofuranosyl-7H-pyrrolo[2,3-d]pyrimidin-4-amine 5'-phosphate.

EXAMPLE 3

7-β-D-Arabinofuranosyl-3,7-dihydro-4H-pyrrolo[2,3-d]pyrimidin-4-one

A solution of one g of 7-β-D-arabinofuranosyl-7H-pyrrolo[2,3-d]pyrimidin-4-amine, 4.3 ml of glacial acetic acid, 50 ml water, and 2.67 g of sodium nitrite is heated at 75° C. for one hour, cooled, and treated with 2.1 g of urea. The solution is evaporated in vacuo and the resulting residue is dissolved in water and treated with 15 ml of wet Dowex 50×8 (in hydrogen form). The resin is filtered and washed with water. The filtrate is treated with charcoal, filtered and evaporated in vacuo. The residue is recrystallized from water to provide 0.75 g of pure 7-β-D-arabinofuranosyl-3,7-dihydro-4H-pyrrolo[2,3-d]pyrimidin-4-one.

EXAMPLE 4

7-β-D-Arabinofuranosyl-3,7-dihydro-4H-pyrrolo[2,3-d]pyrimidin-4-one 5'-Phosphate A mixture of 4 g of 7β-D-arabinofuranosyl-3,7-dihydro-4H-pyrrolo[2,3-d]pyrimidin-4-one, 40 ml of triethyl phosphate, and 3.0 g of phosphoryl chloride is stirred at 0°-5° C. for 3 hours at which point an additional 2.0 g of phosphoryl chloride is added and stirring is continued for 2 hours. The solution is poured onto 150 ml of crushed ice and the pH is adjusted by addition of solid sodium hydrogen carbonate until it stabilizes at pH 5-6. The solution is extracted with chloroform and concentrated in vacuo until crystallization begins. Water is added to achieve a solution and the pH is readjusted to 6-7 with solid sodium hydrogen carbonate. The solution is placed on a Dowex 1×2 50-100 mesh (formate) column (200 ml of wet resin) and is washed with water until the eluate is salt-free. Gradient elusion (water to 0.05 M formic acid) gives the pure product. Appropriate fractions are evaporated in vacuo, keeping the temperature below 30° C., to a small volume. Addition of hot ethanol, until the cloud point is obtained, allows crystallization of the product to proceed. The crystals are filtered, washed with ethanol, and dried to provide pure 7-β-D-arabinofuranosyl-3,7-dihydro-4H-pyrrolo[2,3-d]pyrimidine-4-one 5'-phosphate.

EXAMPLE 5

7-(2,3,5-Tri-O-acetyl-β-D-arabinofuranosyl)-7H-pyrrolo-[2,3-d]pyrimidin-4-amine A solution of 1.5 g of 7-β-D-arabinofuranosyl-7H-pyrrolo[2,3-d]pyrimidin-4-amine, 1.9 g of acetic anhydride, 67 ml of pyridine and 37 mg of p-dimethylaminopyridine is stirred at 0° C. for 6 hours, treated with 50 ml of ethanol, and evaporated in vacuo. The residue is coevaporated with xylenes, dissolved in ethyl acetate, extracted with water, and dried with MgSO₄. Recrystallization of the dried residue from ethanol provides 7-(2,3,5-tri-O-acetyl-β-D-arabinofuranosyl)-7H-pyrrolo[2,3-d]pyrimidin-4-amine.

EXAMPLE 6

7-β-D-Arabinofuranosyl-3,7-dihydro-4H-pyrrolo[2,3-d]pyrimidine-4-thione

A solution of 3.0 g of 7-β-D-arabinofuranosyl-3,7-dihydro-4H-pyrrolo[2,3-d]pyrimidine-4-one, eight ml of acetic anhydride, 150 ml of pyridine, and 50 mg of p-dimethylaminopyridine is stirred at room temperature for 24 hours, evaporated in vacuo, co-evaporated with xylenes, and distributed between ethyl acetate and water. The ethyl acetate layer is washed with saturated NaHCO₃ and dried with MgSO₄. Removal of the ethyl acetate provides 7-(2,3,5-tri-O-acetyl-β-D-arabinofuranosyl)-3,7-dihydro-4H-pyrrolo[2,3-d]pyrimidin-4-one. This is dissolved in 150 ml of dry pyridine, treated with 8.8 g of phosphorus pentasulfide, and heated under reflux for 5 hours. The pyridine is removed in vacuo and the residue is treated with water. The precipitate is filtered, washed with water, and recrystallized from ethanol to afford 7-(2,3,5-tri-O-acetyl-β-D-arabinofuranosyl)-3,7-dihydro-4H-pyrrolo-[2,3-d]pyrimidine-4-thione. A solution of 5.0 g of 7-(2,3,5-tri-O-acetyl-β-D-arabinofuranosyl)-7H-pyrrolo[2,3-d]pyrimidine-4-thione, 200 ml of methanol, and 54 mg of sodium methalate is heated under reflux for 2 hours and treated with IRC-50 ion exchange resin. The filtrate is evaporated in vacuo and the resulting residue is recrystallized from ethanol-water to provide 7-β-D-arabinofuranosyl-3,7-dihydro-4H-pyrrolo[2,3-d]-pyrimidine-4-thione.

EXAMPLE 7

7-β-D-Arabinofuranosyl-7H-pyrrolo[2,3-d]pyrimidine

A mixture of 5 g of 7-β-D-arabinofuranosyl-3,7-dihydro-4H-pyrrolo[2,3-d]pyrimidine-4-thione, 5 g of Raney nickel, and 250 ml of water is stirred and heated under reflux for one hour and filtered while hot. The filtrate is evaporated in vacuo to a small volume and cooled to provide pure 7-β-D-arabinofuranosyl-7H-pyrrolo[2,3-d]pyrimidine.

7-β-D-Arabinofuranosyl-7H-pyrrole[2,3-d]pyrimidine is also obtained by hydrogenolysis of 4-chloro-7-(2,3,5-tri-O-benzyl-β-D-arabinofuranosyl)-7H-pyrrolo[2,3-d]-pyrimidine or 4-chloro-2-methylmercapto-7-(2,3,5-tri-O-benzyl-β-D-arabinofuranosyl)-7H-pyrrolo[2,3-d]-pyrimidine.

EXAMPLE 8

7-β-D-Arabinofuranosyl-7H-pyrrolo[2,3-d]pyrimidine-2,4-diamine

4-Chloro-2-methylsulfonyl-7-(2,3,5-tri-O-benzyl-β-D-arabinofuranosyl)-7H-pyrrolo[2,3-d]pyrimidine. A solution of 10 g of 4-chloro-2-methylmercapto-7-(2,3,5-tri-O-benzyl-β-D-arabinofuranosyl)-7H-pyrrolo-[2,3-d]pyrimidine, 200 ml of ethyl acetate, and 3.5 g of m-chloroperbenzoic acid is heated under reflux for one hour, cooled, and extracted with saturated sodium carbonate. The dried ethyl acetate solution is reduced to a small volume and placed on a column of silica gel. Elution with ethyl acetate provided 8.9 g of 4-chloro-2-methylsulfonyl-7-(2,3,5-tri-O-benzyl-β-D-arabinofuranosyl)-7H-pyrrolo[2,3-d]pyrimidine.

2,4-Dihydrazino-7-(2,3,5-tri-O-benzyl-β-D-arabinofuranosyl)-7H-pyrrolo[2,3-d]pyrimidine.

A mixture of 5 g of 4-chloro-2-methylsulfonyl-7-(2,3,5-tri-O-benzyl-β-D-arabinofuranosyl)-7H-pyrrolo[2,3-d]pyrimidine and 25 ml of anhydrous hydrazine is heated under reflux and nitrogen for two hours, evaporated in vacuo, and co-evaporated with xylenes. The residue is distributed between a mixture of ethyl acetate and water; the aqueous layer is reextracted with ethyl acetate and the combined, dried extracts are evaporated in vacuo to provide crude product. Chromatography of this material over silica gel with (4:1) chloroform-methanol provides 2.3 g of pure 2,4-dihydrazino-7-(2,3,5-tri-O-benzyl-β-D-arabinofuranosyl)-7H-pyrrolo[2,3-d]pyrimidine.

7-β-D-Arabinofuranosyl-7H-pyrrolo[2,3-d]-pyrimidine-2,4-diamine.

A mixture of 12 g of 2,4-dihydrazine-7-(2,3,,5-tri-O-benzyl-β-D-arabinofuranosyl)-7H-pyrrolo[2,3-d]pyrimidine, 250 ml of ethanol, and 25 g of Raney nickel is heated under reflux and nitrogen with stirring for two hours, filtered, and the filtrate evaporated in vacuo. The residue is dissolved in 500 ml of liquid ammonia and then treated portionwise with 0.5 g sodium. The suspension is stirred for one hour, treated with 1.40 g of ammonium chloride, and evaporated in a stream of nitrogen. The residue is washed with ether, cold water, and recrystallized from water to provide pure 7-β-D-arabinofuranosyl-7H-pyrrolo[2,3-d]pyrimidine-2,4-diamine.

EXAMPLE 9

7-β-D-Arabinofuranosyl-7H-pyrrolo[2,3-d]-pyrimidine-2,4-diamine 5'-Phosphate A mixture of 4 g of 7β-arabinofuranosyl-7H-pyrrolo[2,3-d]pyrimidine-2,4-diamine, 40 ml of triethyl phosphate, and 3.0 g of phosphoryl chloride is stirred at 0° C. to 5° C. for 3 hours at which time an additional one g of phosphoryl chloride is added and stirring at 5° C. is continued for 3 hours. The solution is poured on 150 ml of crushed ice and the pH is adjusted by the addition of solid sodium hydrogen carbonate until it stabilizes at pH 5-6. The solution is extracted with chloroform and concentrated in vacuo until crystallization begins. Water is added to achieve solution and the pH is again adjusted to pH 6-7 with sodium hydrogen carbonate. The solution is placed on a Dowex 1×2, 50-100 mesh (formate) column (200 ml of wet resin) and is washed with water until the eluate is salt-free. Gradient elution (water to 0.01 M formic acid) gives the pure product. The appropriate fractions are evaporated in vacuo, keeping the temperature below 30° C., to a small volume. Addition of hot ethanol until the cloud point is obtained allows crystallization to proceed several hours later to provide 7-β-D-arabino-furanosyl-7H-pyrrolo[2,3-d]pyrimidine-2,4-diamine 5'-phosphate.

EXAMPLE 10

2-Amino-7-β-D-arabinofuranosyl-3,7-dihydro-4H-pyrrolo[2,3-d]pyrimidin-4-one

4-Allyloxy-2-methylsulfonyl-7-(2,3,5-tri-O-benzyl-β-D-arabinofuranosyl)-7H-pyrrolo[2,3-d]pyrimidine.

A solution of 10 g of 4-chloro-2-methyl-sulfonyl-7-(2,3,5-tri-O-benzyl-β-D-arabinofuranosyl)-7H-pyrrolo[2,3-d]pyrimidine, 1.35 g of sodium allyloxide, and 50 ml of DMF is stirred at ambient temperature for 24 hours, evaporated in vacuo and coevaporated with xylenes. The residue is distributed between a mixture of ethyl acetate and water and the dried ethyl acetate extracts are evaporated in vacuo to provide crude product. Chromatography of this material over silica gel with ethyl acetate provides pure 4-allyloxy-2-methylsulfonyl-7-(2,3,5-tri-O-benzyl-β-D-arabino-furanosyl)-7H-pyrrolo[2,3-d]pyrimidine.

2-Amino-4-allyloxy-7-(2,3,5-tri-O-benzyl-β-D-arabinofuranosyl)-7H-pyrrolo[2,3-d]pyrimidine.

A mixture of 13.5 g of 4-allyloxy-2-methylsulfonyl-7-(2,3,5-tri-O-benzyl-β-D-arabinofuranosyl)-7H-pyrrolo-[2,3-d]pyrimidine and 250 ml of liquid ammonia is heated at 100° C. for 2 hours and allowed to evaporate in a stream of nitrogen. The residue is dissolved in ethyl acetate and chromatographed over silica gel with ethyl acetate to provide 9.3 g of pure 2-amino-4-allyloxy-7-(2,3,5-tri-O-benzyl-β-D-arabinofuranosyl)-7H-pyrrolo[2,3-d]pyrimidine.

2-Amino-7-β-D-arabinofuranosyl-3,7-dihydro-4H-pyrrolo[2,3-d]pyrimidin-4-one.

A mixture of 8.0 g of 2-amino-4-allyloxy-7-(2,3,5-tri-O-benzyl-β-D-arabino-furanosyl)-7H-pyrrolo[2,3-d]pyrimidine, 1.5 g of 20% palladium on charcoal, 6.7 ml of acetic acid, and 150 ml of methoxy ethanol is hydrogenated at 50° C. and approximately 3 atmospheres until the uptake of hydrogen ceases. The mixture is filtered, evaporated in vacuo, dissolved in water, and treated with 60 ml of wet IR-45 ion exchange resin. The filtrate is concentrated to dryness in vacuo and the residue is recrystallized from water to provide pure 2-amino-7-β-D-aminofuranosyl-3,7-dihydro-4H-pyrrolo[2,3-d]pyrimidin-4-one.

EXAMPLE 11

2-Amino-7-β-D-arabinofuranosyl-3,7-dihydro-4H-pyrrolo[2,3-d]pyrimidin-4-one 5'-Phosphate A mixture of 5.2 g of 2-amino-7-β-arabino-furanosyl-3,7-dihydro-4H-pyrrolo[2,3-d]pyrimidin-4-one, 12 g of phosphoryl chloride, and 50 ml of triethyl phosphate is stirred at 0°-5° C. for 3 hours. The solution is added dropwise to a vigorously stirred flask of anhydrous ether (1000 ml). The ether is decanted and additional ether (600 ml) is added to the beige precipitate. After stirring for 0.5 hour, the ether is decanted, and this procedure is repeated once more with additional ether (600 ml). The precipitate is filtered, washed with ether, and then dissolved in about 120 g of ice water. The aqueous solution is allowed to stand at room temperature overnight, adjusted to pH 8 with 1 N sodium hydroxide, and placed on a column of Bio-Rad AG 1×8 (in the formate form, 50-100 mesh, 60 ml of wet resin).

After washing with water (600 ml), the column is eluted with a gradient of 0.2 to 0.5 M formic acid (1000 ml each). Fractions containing the product are pooled and reduced to a small volume in vacuo. Addition of ethanol precipitated crude product which is filtered, washed with ethanol and then ether, and dried under vacuum at 80° C. for 2 hours to provide 2-amino-7-β-D-arabinofuranosyl-3,7-dihydro-4H-pyrrolo[2,3-d]pyrimidine-4-one 5'-phosphate.

I claim:

1. An improved process for producing a compound of the formula

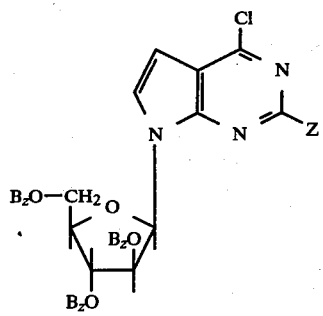

wherein Z is hydrogen or methylmercapto which comprises glycosylating 4-chloro-7H-pyrrolo[2,3-d]pyrimidine with 2,3,5-tri-O-benzyl-α-D-arabinofuranosyl chloride wherein the improvement comprises treating 4-chloro-7H-pyrrolo-[2,3-d]pyrimidin with sodium hydride in a suitable solvent to form the anion having the formula

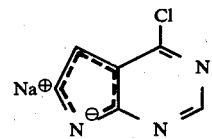

and β-D-arabinofuranosylating said anion with 2,3,5-tri-O-benzyl-α-D-arabinofuranosyl chloride.

* * * * *